United States Patent [19]

Winter

[11] Patent Number: 4,474,472
[45] Date of Patent: Oct. 2, 1984

[54] ARRANGEMENT FOR THE DETECTION OF PARTICLES IN A GAS FLOW

[75] Inventor: Hans Winter, Munich, Fed. Rep. of Germany

[73] Assignee: Siemens Aktiengesellschaft, Berlin & Munich, Fed. Rep. of Germany

[21] Appl. No.: 288,940

[22] Filed: Jul. 31, 1981

[30] Foreign Application Priority Data

Aug. 12, 1980 [DE] Fed. Rep. of Germany ....... 3030499

[51] Int. Cl.³ ............................................. G01N 21/01
[52] U.S. Cl. ..................................... 356/438; 356/38; 356/440
[58] Field of Search ................. 356/38, 432, 438, 439, 356/440, 445

[56] References Cited

U.S. PATENT DOCUMENTS 2,489,286 11/1949 Grant ..................................... 356/38
3,795,025 3/1974 Sadamitsu ........................ 15/256.52

FOREIGN PATENT DOCUMENTS 2654726 3/1978 Fed. Rep. of Germany.

OTHER PUBLICATIONS

Crosse et al., "Instrument for Recording the Dust Nuisance Emitted by Chimneys" *Journal of Scientific Instruments*, vol. 38 (Jan. 1961), pp. 12–17.

*Primary Examiner*—R. A. Rosenberger
*Attorney, Agent, or Firm*—Hill, Van Santen, Steadman & Simpson

[57] ABSTRACT

A measuring system for the detection of particles in a gas flow utilizes a light source, a light detector for receiving light from the light source, and an evaluating circuit connected to the light detector. A hollow body having a longitudinal portion and a side portion which branches off from the longitudinal portion at an angle is provided. One end of the longitudinal portion is open for entry of the gas flow and an end of the side portion is open for exiting of the gas flow. The other end of the longitudinal portion is closed with a cover in which the light source and light detector means are arranged. Particles which might be present in the gas are deposited on inner walls of a bore hole in the cover so as to change detected intensity of the light from the light source which passes through soiled areas at the inner wall of the bore hole.

1 Claim, 4 Drawing Figures

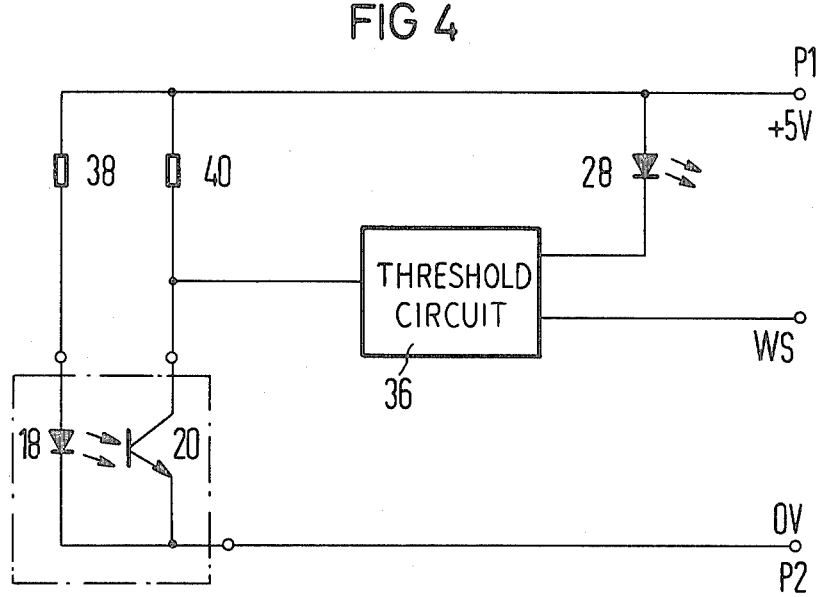

4,474,472

ARRANGEMENT FOR THE DETECTION OF PARTICLES IN A GAS FLOW

BACKGROUND OF THE INVENTION

The invention refers to an arrangement for the detection of particles in a gas flow whereby a measuring device is provided which responds to the presence of particles. A light source is provided together with a light detector which receives the light proceeding from the light source. This light is influenced by the particles so as to control a connected evaluating circuit.

An arrangement of this sort is necessary, for example, in the case of non-mechanical fast printers with an electrophotographic printing principle. There, the residual toner, which, after the printing, is still located on the photoconductor drum, must be sucked off and caught in a paper filter (see, for example, U.S. Pat. No. 3,795,025, incorporated herein by reference). The filter must be monitored so that in the case of a defect, the printer is immediately disconnected and no toner gets into the environment of the printer with the exhaust air. Thus, an arrangement is necessary with which it can be determined whether particles are contained in the gas flow behind the filter.

An arrangement of this sort is known from German LP No. 2,654,726, incorporated herein by reference. There, a probe constructed of a light-permeable hollow body is arranged in the gas flow. In the hollow body, there is a light source which illuminates the hollow body on the side of the wall upon which the gas flow strikes and upon which particles contained in the gas flow settle. In the hollow body there is a light detector upon which the light reflected on this side of the wall strikes. The light detector releases a signal which is proportional to the reflected light intensity. This signal can then be further evaluated. A disadvantage of this arrangement is that it is not very precise.

SUMMARY OF THE INVENTION

An object of this invention is to provide an arrangement for the detection of particles in a gas flow which displays a high sensitivity. This problem is solved by providing a hollow body which has a longitudinal part or portion and a side part or portion which branches off from the longitudinal portion at an angle. One end of the longitudinal portion is opened for the entry of the gas flow, the end of the side portion is opened for exiting of the gas flow, and the other end of the longitudinal portion is closed with a cover in which the measuring device is arranged.

The gas flow is thus conveyed in a curved path through the hollow body. The centrifugal forces which occur also act upon particles which may be present and guide them to the other end of the longitudinal part of the hollow body. There, a depression in the form of a bore hole can be provided at which the light source and the light detector is arranged which together form a light barrier. The bore hole can be closed with a screw. With the help of the light barrier, soiling in the bore hole is monitored.

It is practical if the light source and the light detector are arranged in a mounting which can be introduced as a part in the cover. It is thereby further possible to arrange the evaluating circuit next to the mounting in the cover. It is further advantageous if a luminescent diode is arranged in the cover which then responds when a case of interference is detected.

The arrangement of the invention has great sensitivity to the presence of particles in the gas flow. By simple removal of the screw in the cover, the measuring device can be cleaned. A further advantage is that the arrangement has a small and inexpensive type of construction.

BRIEF DESCRIPTION OF THE DRAWINGS

FIG. 4 shows an evaluating circuit for use in the invention.

DESCRIPTION OF THE PREFERRED EMBODIMENTS

Figure 1:
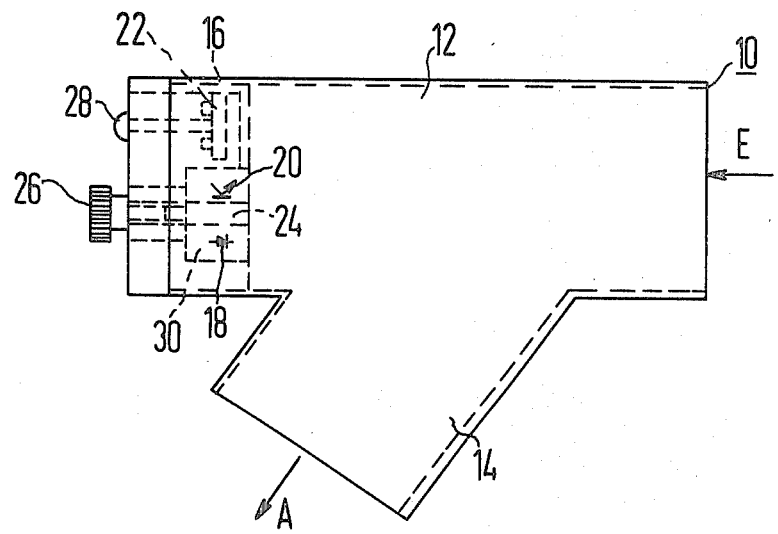
FIG. 1 shows the structure of an arrangement for the detection of particles in a gas flow according to the invention.

Corresponding to FIG. 1, the arrangement has a hollow body 10 which is comprised of a longitudinal portion or part 12 and a side portion or part 14 which branches off from the longitudinal part 12 at an angle. The gas flow enters in one end E of the longitudinal part 12 into the hollow body 10, is guided through the hollow body in a bent path to the side part 14, and there exits at exit location A.

The other end of the longitudinal part 12 is closed with a cover 16. Arranged in the cover 16 is a measuring unit. This unit comprises a light source 18, a light detector 20 and an evaluating circuit 22. The light source 18 and the light detector 20 are arranged at an inner wall of a bore hole 24 on opposite sides of the hole 24. The bore hole 24 is open at one end toward the gas entry E of the hollow body 10, and on the opposite side it is closed with a screw 26. The light source 18 and the light detector 20 thus form a light barrier which monitors the content of the bore hole 24.

If a gas flow with particles is deflected from the entry E in a curved path to the exit A, then the centrifugal forces occurring act upon the particles and guide these to the cover 16 and thus also into the bore hole 24. There, they deposit on the inner wall. The light barrier, comprised of the light source 18 and the light detector 20, evaluates the thickness of the deposit of the particles on the inner wall of the bore hole 24 which is preferably translucent at this location. Of course apertures could also be provided at the inner wall of the bore hole with the light detector and light source being flush with the inner wall. The light detector 20 releases a signal which is proportional to the thickness of the deposit fed to the evaluating circuit 22. When this signal exceeds a specific threshold value, a warning signal is generated by the evaluating circuit. This warning signal can, for example, be directed to a luminescent diode 28 which also is arranged in the cover 16 and which lights up in case of the appearance of the warning signal.

Figure 3:
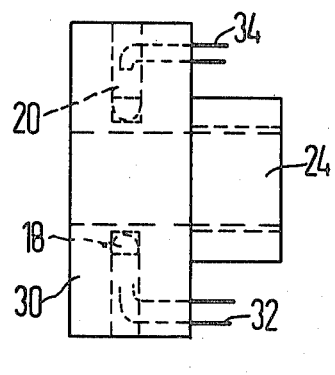
FIG. 3 shows a reversed side view of the mounting of FIG. 2.
Figure 2:
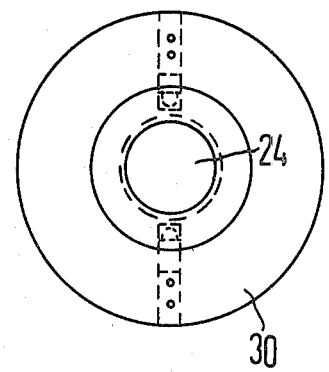
FIG. 2 shows a front view from a gas entry end of the system of a mounting for the light barrier.

The light source 18 and the light detector 20 can be arranged in a special mounting 30 inserted or received in the cover 16. The mounting 30 is depicted in FIGS. 2 and 3 in a larger scale. The mounting is provided with the bore hole 24 into which the screw can be screwed on the one side. The bore hole 24, as was already explained, passes through between the light source 18 and the light detector 20. The lead wires 32 of the light source 18 and the lead wires 34 of the light detector 20 lead from the mounting 30 directly to the evaluating circuit 22.

A preferred embodiment of the evaluating circuit 22 is depicted in FIG. 4. Between two operating potential connections P1 and P2 there is the series connection of a resistor 38 with the light source 18, for example a luminescent diode. Parallel to this is a series connection of a resistor 40 and the light detector 20, for example a phototransistor. The connection point between the resistor 40 and the light detector 20 is connected with a threshold circuit 36 of known structure. The threshold circuit 36 monitors the output signal of the light detector 20 and releases a warning signal WS at the output when the signal exceeds a set threshold value. Simultaneously, the luminescent diode 28 can be activated which lights up for this case. The warning signal WS at the output can in addition be used for switching off the device to be monitored. The sensitivity of the measuring device can be determined with the help of the resistor 40.

The measuring device can be cleaned in a simple manner. For this it is necessary that the screw 26 be unscrewed and the bore hole 24 which has been opened is cleaned with a cleaning brush. Accordingly, simultaneously a testing of function is undertaken. When the cleaning brush passes through the light barrier, the luminescent diode 28 must light up and again extinguish after the removal of the brush.

Although various minor modifications may be suggested by those versed in the art, it should be understood that I wish to embody within the scope of the patent warranted hereon, all such embodiments as reasonably and properly come within the scope of my contribution to the art.

I claim as my invention:

1. A measuring system for the detection of particles in a gas flow, comprising: a light source; a light detector means for receiving light from the light source after influencing by the particles; an evaluating means connected to the light detector means; a hollow body having a longitudinal portion and a side portion which branches off from a side wall of the longitudinal portion prior to an end thereof at an angle, one end of the longitudinal portion being opened for entry of the gas flow, an end of the side portion being opened for exiting of the gas flow, and an other end of the longitudinal portion being closed with a cover having a surface portion centrally of the longitudinal portion side walls on which the particles travelling along the longitudinal portion may be deposited and at which the light source and light detector means are positioned such that the deposited particles to be detected at least partially affect the light being detected; the light source and the light detector means being arranged next to a bore hole in the cover such that a light beam passes through the bore hole and is influenced by particles deposited on an inner side wall of the bore hole, and the bore hole being open to the air flow such that the particles are deposited on the inner side wall of the hole; and the bore hole being closed at an external surface of the cover with a removable screw which can be removed for cleaning the side wall of the bore hole.

* * * * *